(12) United States Patent  
Gibertoni

(10) Patent No.: US 6,904,911 B2
(45) Date of Patent: Jun. 14, 2005

(54) DISPOSABLE ACTIVE HUMIDIFIER FOR THE MECHANICAL VENTILATION OF A PATIENT

(75) Inventor: Lucio Gibertoni, Mirandola (IT)

(73) Assignee: Mallinckrodt Inc., St. Louis, MO (US)

( * ) Notice: Subject to any disclaimer, the term of this patent is extended or adjusted under 35 U.S.C. 154(b) by 50 days.

(21) Appl. No.: 10/364,227

(22) Filed: Feb. 11, 2003

(65) Prior Publication Data

US 2003/0127095 A1 Jul. 10, 2003

Related U.S. Application Data

(63) Continuation of application No. 10/331,362, filed on Dec. 30, 2002, now abandoned, which is a continuation of application No. 09/673,594, filed as application No. PCT/US99/08699 on Apr. 21, 1999, now Pat. No. 6,510,848.

(30) Foreign Application Priority Data

Apr. 22, 1998 (IT) .......................................... MI98A0862

(51) Int. Cl.[7] .............................................. A62B 18/08
(52) U.S. Cl. ............................ 128/201.13; 128/203.16; 128/203.17; 261/101; 261/104
(58) Field of Search ....................... 128/201.13, 203.16, 128/203.17; 261/101, 104

(56) References Cited

U.S. PATENT DOCUMENTS

| 3,228,876 A | 1/1966 | Mahon |
| 3,927,981 A | 12/1975 | Vinnay et al. |
| 4,031,012 A | 6/1977 | Gics |
| 4,086,305 A | 4/1978 | Dobritz |
| 4,098,852 A | 7/1978 | Christen et al. |
| 4,146,597 A | 3/1979 | Eckstein et al. |
| 4,155,961 A | 5/1979 | Benthin |
| 4,381,267 A | 4/1983 | Jackson |
| 4,449,992 A | 5/1984 | Yamada et al. |
| 4,859,331 A | 8/1989 | Sachtler et al. |
| 4,910,384 A | 3/1990 | Silver |
| 5,192,499 A | 3/1993 | Sakai et al. |
| 5,195,515 A | 3/1993 | Levine |
| 6,510,848 B1 * | 1/2003 | Gibertoni ............... 128/201.13 |

* cited by examiner

Primary Examiner—Glenn K. Dawson
Assistant Examiner—Darwin P Erezo
(74) Attorney, Agent, or Firm—Fulwider Patton Lee & Utecht, LLP

(57) ABSTRACT

A disposable active humidifier for the mechanical ventilation of a patient, which has the particularity that it comprises a cartridge which forms a humidification chamber which is delimited by an inlet and by an outlet and can be interposed in the ventilation circuit. The cartridge has an interspace which is externally delimited by a heat exchange surface and is internally delimited by a hydrophobic membrane which surrounds the humidification chamber. A humidification fluid, originating from a bottle or bag, can be introduced in the interspace.

3 Claims, 2 Drawing Sheets

DISPOSABLE ACTIVE HUMIDIFIER FOR THE MECHANICAL VENTILATION OF A PATIENT

RELATED APPLICATIONS

This is a continuation of Ser. No. 10/331,362 filed Dec. 30, 2002, abandoned, which is a continuation of Ser. No. 09/673,594 filed Oct. 18, 2000, now U.S. Pat. No. 6,510, 848, which is the U.S. national phase of PCT international application No. PCT/US99/08699 filed Apr. 21, 1999, which claims priority from Italian Application No. MI98 A 000862 filed Apr. 22, 1998.

The present invention relates to a disposable active humidifier for the mechanical ventilation of a patient.

It is known that the mechanical ventilation of a patient uses dry gases which are humidified before being inspired by the patient. Most commercially available systems are based on the principle of making the gas flow directly over the water contained in a heated container.

The conventional solution has a drawback which is constituted by the relatively high volume of the cartridge, which constitutes an additional bulk; it should be noted that it is very important to reduce bulk, since in mechanical ventilation, in which the pressure of the ventilator expands the lungs of the patient to ventilate him, an extra compressible space is certainly a negative factor.

The aim of the invention is indeed to eliminate the drawbacks mentioned above, which are typical of conventional systems (bacterial contamination and high compressible volume), by providing a disposable active humidifier for the mechanical ventilation of a patient which has a very small bulk and in particular constitutes an integrated segment in the ventilation circuit and in practice therefore does not increase the volume of compressible air.

Within the scope of this aim, a particular object of the invention is to provide a disposable active humidifier which can be prepared in a sterile package which can be connected only once to the patient without requiring further handling with the risk of bacterial contamination.

Another object of the present invention is to provide an active humidifier in which the water remains confined within the cartridge with a continuous supply which in practice forms a closed circuit with no need for connection to the outside.

Another object of the present invention is to provide a disposable active humidifier which, by virtue of its particular constructive characteristics, is capable of giving the greatest assurances of reliability and safety in use.

This aim, these objects and others which will become apparent hereinafter are achieved by a disposable active humidifier for the mechanical ventilation of a patient, according to the invention, characterized in that it comprises a cartridge which forms a humidification chamber which is delimited by an inlet and by an outlet and can be interposed in a ventilation circuit, said cartridge having an interspace which is externally delimited by a heat exchange surface and is internally delimited by a hydrophobic membrane which surrounds said humidification chamber, a humidification fluid being introducible in said interspace.

Further characteristics and advantages will become apparent from the description of a preferred but not exclusive embodiment, illustrated only by way of non-limitative example with the aid of the accompanying drawings, wherein.

Figure 1:
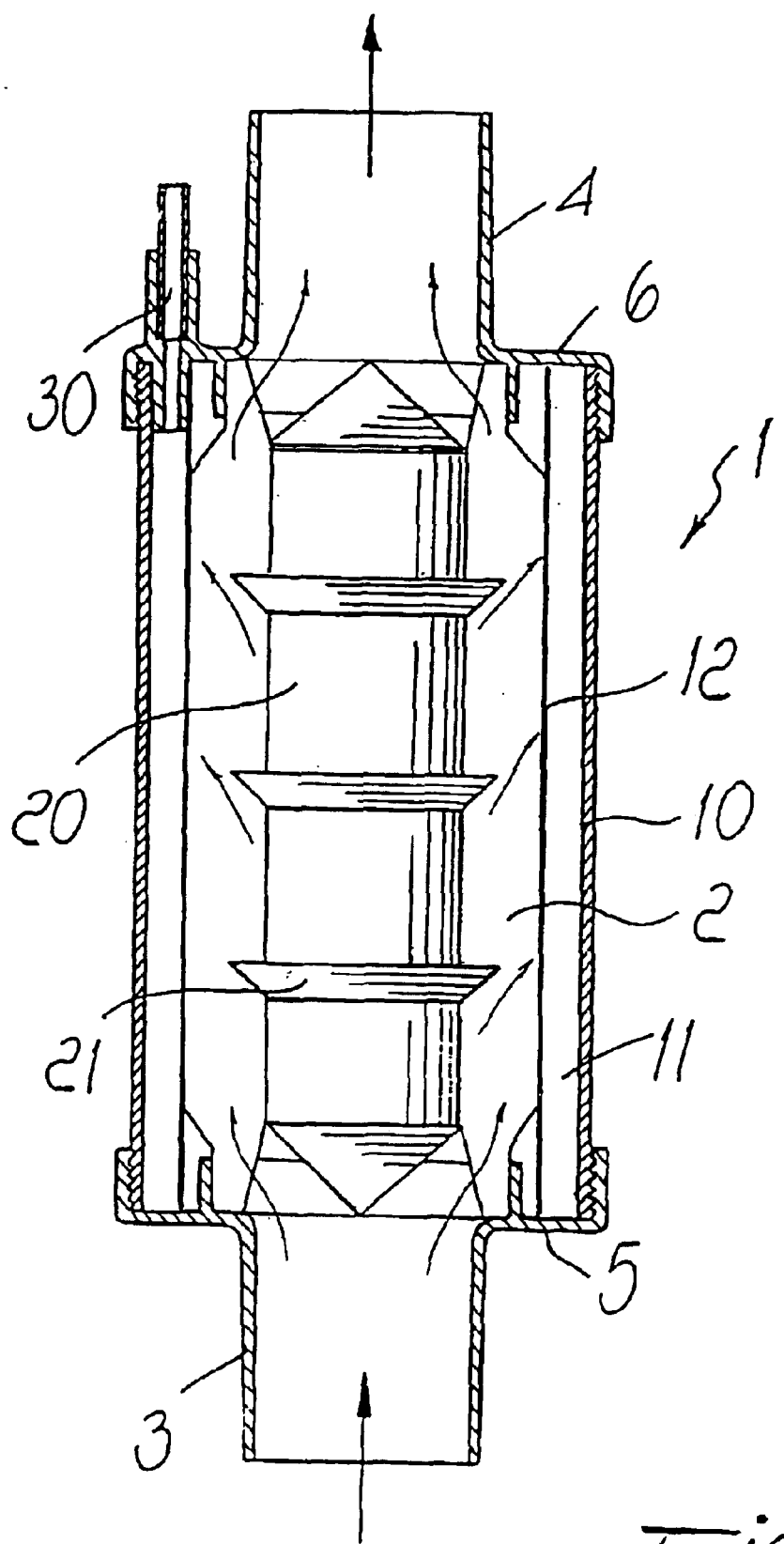
FIG. 1 is a schematic sectional view of a disposable active humidifier according to the invention.

With reference to the above figures, the disposable active humidifier for the mechanical ventilation of a patient comprises a cartridge, generally designated by the reference numeral 1, which internally forms a humidification chamber 2 which is delimited by an inlet 3 and by an outlet 4 which are formed on respective caps 5 and 6 which are arranged mutually opposite at the axial ends of the humidification chamber 2.

The cartridge 1 is externally provided with a heat exchange surface, advantageously constituted by a tubular aluminum casing 10, which delimits an interspace 11 formed by a hydrophobic membrane 12 which delimits the humidification chamber 2.

Inside the humidification chamber 2 there is a diffuser 20 which is meant to direct the incoming air stream so that it flows over the membrane 12, so as to facilitate the transfer of humidity through the hydrophobic membrane 12 that delimits the interspace 11, inside which water is introduced by means of an inlet 30, to which it is possible to connect a simple bag or bottle which continuously introduces the water into the interspace so that by means of the hydrophobic membrane it is possible to ensure the required degree of humidity of the air.

It should be added that the diffuser advantageously has protrusions 21 shaped like a conical inclined surface, spaced apart from the membrane, which facilitate the conveyance of the air stream against the membrane, which provides a barrier against bacteria, so that the system can be supplied with ordinary distilled water, thus reducing the operating costs.

The cartridge 1 can be easily used in a ventilation circuit, designated schematically by the reference numeral 40 in the drawing, in which there is a heater 41 which forms the seat for accommodating the external casing of the cartridge.

From the above description it is thus evident that the invention achieves the intended aim and objects, and in particular the fact is stressed that the particular structure that has been used allows to provide a disposable active humidifier which in practice does not increase the volume of air present in the ventilation circuit, since it provides a simple segment which is interposed in the ventilation circuit itself.

Furthermore, the new active humidifier is based on an innovative principle which is different from the other systems that are commercially available, since its humidification principle is based on the vaporization of water instead of on flowing over water present in a heated container.

The present system uses a humidifier cartridge which is integrated in the temperature-controlled ventilation circuit and which by vaporization charges the dry gases on the inspiratory line of the patient with humidity.

By virtue of the PVC temperature-controlled circuit in which the heating resistor is embedded in the external reinforcement spiral, the humidity released by the humidifier cartridge does not condense along the inspiratory line but is transferred in full to the patient.

The cartridge of the humidifier (see FIG. 1) is constituted by an external body made of metal (aluminum) which acts as interface with the heating element of the humidifier. Inside the cartridge there is a hydrophobic membrane which provides the interface between the liquid and the vapor phase of the inspiratory line.

The hydrophobic membrane allows the passage of the vapor that forms as a consequence of the heating of the water contained in the cartridge.

The system can be supplied with ordinary sterile/double-distilled water.

Figure 2:
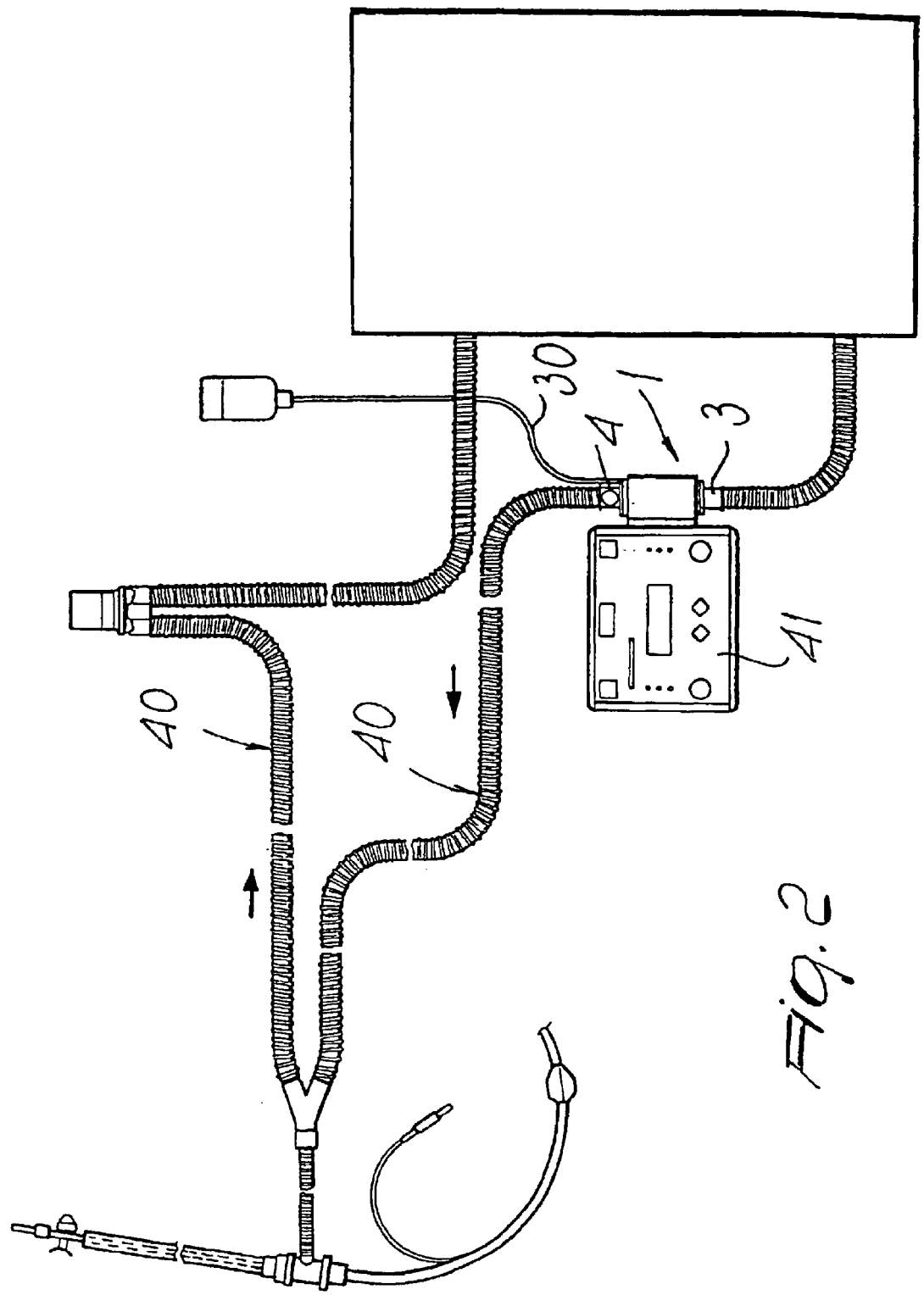
FIG. 2 is a schematic view of the active humidifier included in a ventilation circuit.

The innovation of the system is that it uses a cartridge which is integrated in the circuit (see the drawing in the accompanying FIG. 2) and is preassembled to the ventilator with the connections provided.

Differently from flow-over humidification systems, the present system eliminates the contact of the supply water with the outside environment, avoiding the risk of exogenous contamination of the patient and keeping the system dry without forming condensate in the ventilation circuit.

The invention thus conceived is susceptible of numerous modifications and variations, all of which are within the scope of the inventive concept.

All the details may furthermore be replaced with other technically equivalent elements.

In practice, the materials used, as well as the contingent shapes and the dimensions, may be any according to the requirements.

What is claimed is:

1. A disposable active humidifier for humidifying an air stream for the mechanical ventilation of a patient, which comprises:

a humidification chamber which is delimited by an inlet and by an outlet and can be interposed in a ventilation circuit for the air stream;

a hydrophobic membrane surrounding said humidification chamber for transferring a humidification fluid through said membrane into said humidification chamber; and a diffuser disposed axially inside said humidification chamber, said diffuser being adapted to direct the air stream of the ventilation circuit against said membrane, the diffuser having inclined rings which are spaced apart from said membrane and are adapted to divert the air stream toward said hydrophobic membrane.

2. A disposable active humidifier according to claim 1, wherein said humidification chamber has a substantially cylindrical shape and forms a segment of said ventilation circuit.

3. A disposable active humidifier according to claim 1, wherein said outlet and said inlet are formed by respective caps which axially delimit said humidification chamber.

* * * * *